US012599764B2

(12) United States Patent
Hansen et al.

(10) Patent No.: US 12,599,764 B2
(45) Date of Patent: Apr. 14, 2026

(54) HEADER ASSEMBLY HAVING CONTROLLED THERAPEUTIC AGENT RELEASE

(71) Applicant: Pacesetter, Inc., Sylmar, CA (US)

(72) Inventors: Joseph Hansen, Los Angeles, CA (US); Wesley Alleman, Santa Clarita, CA (US); Keith Victorine, Santa Clarita, CA (US); Bei Ning Zhang, Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 1076 days.

(21) Appl. No.: 17/555,217

(22) Filed: Dec. 17, 2021

(65) Prior Publication Data

US 2022/0347467 A1 Nov. 3, 2022

Related U.S. Application Data

(60) Provisional application No. 63/182,687, filed on Apr. 30, 2021.

(51) Int. Cl.
*A61N 1/05* (2006.01)

(52) U.S. Cl.
CPC .................................. *A61N 1/0568* (2013.01)

(58) Field of Classification Search
CPC ................ A61N 1/37205; A61N 1/375; A61N 1/37512; A61N 1/3752; A61N 1/3754; A61N 1/3756; A61N 1/3758; A61N 1/0568; A61N 1/0575
See application file for complete search history.

(56) References Cited

U.S. PATENT DOCUMENTS

| 2016/0228716 | A1 | 8/2016 | Schmidt et al. | |
| 2019/0134413 | A1* | 5/2019 | Mar .................... | A61N 1/37205 |
| 2019/0351222 | A1* | 11/2019 | Strang ................. | A61N 1/0575 |
| 2020/0129763 | A1 | 4/2020 | Paspa et al. | |
| 2020/0289835 | A1 | 9/2020 | Eby et al. | |

(Continued)

FOREIGN PATENT DOCUMENTS

CN          111686373 A          9/2020

OTHER PUBLICATIONS

Notice of Intent to Grant from related EP Application No. 22170416.6, mailed on Nov. 11, 2024 (6 pages).

(Continued)

*Primary Examiner* — Benjamin J Klein
*Assistant Examiner* — Daniel Tehrani
(74) *Attorney, Agent, or Firm* — WOMBLE BOND DICKINSON (US) LLP

(57) ABSTRACT

A leadless biostimulator, such as a leadless pacemaker, including a header assembly having a monolithic controlled release device (MCRD) for therapeutic agent elution, is described. The MCRD is in fluid communication with a space between an insulator and an electrode of the header assembly to elute therapeutic agent into the space when the leadless biostimulator is implanted. The therapeutic agent can elute through the space around the electrode to provide controlled elution of the therapeutic agent to a surrounding environment. The electrode can extend longitudinally through the insulator cavity to a distal tip that provides a stable surface area and controlled impedance for pacing a target tissue. Other embodiments are also described and claimed.

20 Claims, 7 Drawing Sheets

(56)          References Cited

U.S. PATENT DOCUMENTS

2021/0228888 A1    7/2021  Zhang et al.
2021/0236814 A1*   8/2021  Anderson  .......... A61N 1/37518

OTHER PUBLICATIONS

Extended European Search Report from related EP Application No. 22170416.6, mailed on Sep. 9, 2022 (9 pages).
First Office Action mailed Dec. 18, 2025 from related Chinese Patent Application No. 202210473535.5, 13 pages including translation.

* cited by examiner

JOIN A FLANGE, AN INSULATOR, AND AN ELECTRODE — 702

MOUNT A MONOLITHIC CONTROLLED RELEASE DEVICE (MCRD) WITHIN AN INSULATOR CAVITY OF THE INSULATOR — 704

MOUNT AN ELECTRODE TIP OR AN ELECTRODE HELIX ON A DISTAL END OF AN ELECTRODE PIN OF THE ELECTRODE — 706

MOUNT A HELIX MOUNT ON THE FLANGE — 708

MOUNT A HELICAL FIXATION ELEMENT ON THE HELIX MOUNT — 710

HEADER ASSEMBLY HAVING CONTROLLED THERAPEUTIC AGENT RELEASE

This application claims the benefit of priority of U.S. Provisional Patent Application No. 63/182,687, filed on Apr. 30, 2021, which is incorporated herein by reference in its entirety to provide continuity of disclosure.

BACKGROUND

Field

The present disclosure relates to biostimulators having header assemblies. More specifically, the present disclosure relates to leadless biostimulators having header assemblies that include an electrode, and methods of manufacturing such header assemblies.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. The pulse generator usually connects to the proximal end of one or more implanted leads through a feedthrough assembly, which creates an isolated electrical pass-through into a hermetic case for pulse/sense transmissions to a target tissue. The feedthrough assembly can be used in low voltage or high voltage applications. A distal end of the implanted leads, which typically have lengths of 50 to 70 centimeters, contains one or more electrodes for positioning adjacent to the inside or outside wall of a cardiac chamber. The leads have an insulated electrical conductor or conductors for connecting the pulse generator to the electrodes in the heart. Accordingly, the pulse generator can deliver a pacing pulse from within a hermetically sealed housing through the feedthrough assembly, the lead, and the electrode to the target tissue.

Conventional pacemakers have several drawbacks, including a risk of lead or feedthrough assembly breakage, complex connections between the leads and the feedthrough assembly, and a risk of infection and morbidity due to the separate leads and pulse generator components. Many of the issues associated with conventional pacemakers are resolved by the development of a self-contained and self-sustainable biostimulator, or so-called leadless biostimulator. The leadless biostimulator can be attached to tissue within a dynamic environment, e.g., within a chamber of a beating heart, to deliver pacing pulses directly to the tissue without the use of leads.

SUMMARY

Existing leadless biostimulators have a hermetically sealed device package containing internal components to generate and receive electrical pulses through an electrode of a header assembly. The electrode can include an enclosed cup containing a therapeutic agent. The cup may be capped, and the therapeutic agent can elute through a hole in the cap of the cup toward a target tissue when the leadless biostimulator is implanted. The capped cup provides a relatively large surface area that may inconsistently contact the target tissue, and thus, may provide inconsistent impedance and electrical pulse control. Furthermore, the small hole in the cap may restrict transport of fluid into the cup or become clogged, and thus, may restrict the elution of therapeutic agent-laden fluid out of the cup. Accordingly, there is a need for a header assembly having greater control over electrode impedance and therapeutic agent release.

A leadless biostimulator including a header assembly for controlled delivery of therapeutic agent around an electrode to a target tissue is described. Methods of manufacturing the header assembly are also described. In an embodiment, the header assembly includes a flange having a flange channel extending along a longitudinal axis. An insulator can be disposed in the flange channel, and can include an insulator cavity. The header assembly can include an electrode that extends longitudinally through the insulator cavity. A space can be formed between the insulator and the electrode. In an embodiment, a monolithic controlled release device (MCRD) is disposed in the insulator cavity such that therapeutic agent elutes from the MCRD into the space when the leadless biostimulator is implanted in blood. The header assembly can include a helical fixation element to affix the biostimulator to a target tissue site. Accordingly, the therapeutic agent can be delivered to the target tissue site upon implantation.

The MCRD can have an annular body. For example, the annular body can be tubular, and can be disposed within the insulator cavity such that a central lumen of the tubular body is aligned with the longitudinal axis of the flange. Accordingly, an electrode pin of the electrode can extend longitudinally through the central lumen. An electrode tip is mounted on a distal end of the electrode pin. Alternatively, an electrode helix may be mounted on the distal end of the electrode pin. The electrode tip and/or electrode helix can be disposed within a helix mount channel of a helix mount that supports the helical fixation element. Furthermore, the electrode tip and/or electrode helix can deliver pacing impulses from the electrode to the target tissue. Accordingly, the therapeutic agent can elute from the MCRD and be delivered between the helix mount and the distal end of the electrode pin to the target tissue at the pacing site.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Figure 1:
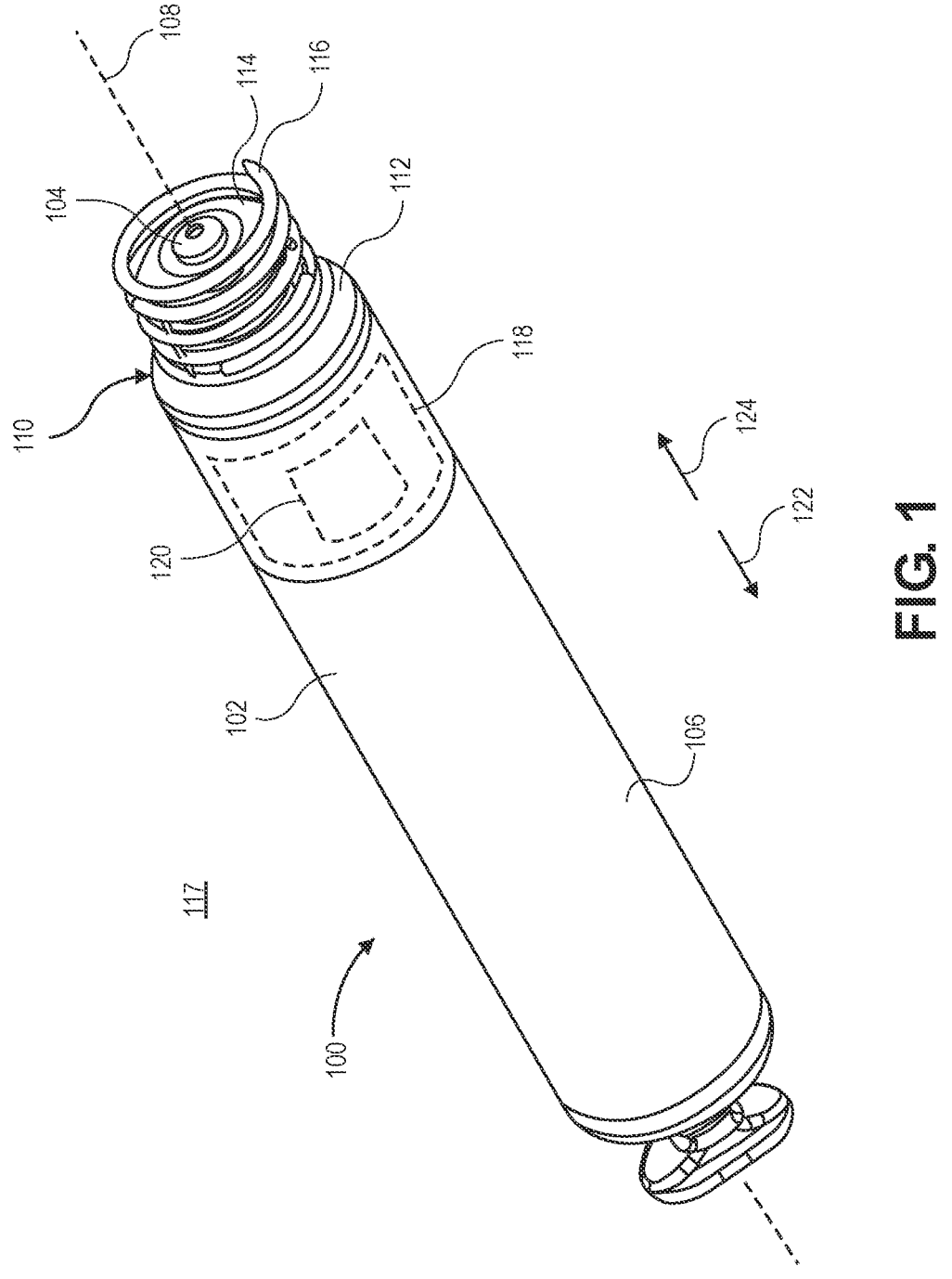
FIG. 1 is a perspective view of a leadless biostimulator, in accordance with an embodiment.

Embodiments of the present disclosure include a leadless biostimulator, e.g., a leadless cardiac pacemaker, having a header assembly that includes a monolithic controlled release device (MCRD) to elute therapeutic agent around an electrode. The leadless biostimulator may be used to pace cardiac tissue, e.g., in the ventricles or the atria of a heart. The leadless biostimulator may be used in other applications, however, such as deep brain stimulation. Thus, reference to the leadless biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a leadless biostimulator. Similarly, "proximal" may indicate a second direction opposite to the first direction. Such terms are provided to establish relative frames of reference, however, and are not intended to limit the use or orientation of a leadless biostimulator to a specific configuration described in the various embodiments below.

In an aspect, a leadless biostimulator includes a header assembly having an electrode extending longitudinally through an insulator cavity of an insulator. A MCRD containing a therapeutic agent can be located within the insulator cavity. For example, the MCRD can be retained within the insulator cavity by a distal tip of the electrode or via a press fit between the MCRD and an electrode helix of the electrode. The retained MCRD can therefore elute the therapeutic agent into the insulator cavity toward a target tissue when the leadless biostimulator is implanted in blood. For example, the therapeutic agent can elute through a space between the insulator and the electrode, and around the electrode through a channel of a helix mount to a surrounding environment. The channel of the helix mount can have sufficient cross-sectional area, e.g., an annular cross-sectional area, to permit blood and therapeutic agent to be exchanged between the MCRD and the surrounding environment. Accordingly, the header assembly described below can provide controlled therapeutic agent release.

In an aspect, the electrode of the header assembly includes an electrode pin to carry pacing pulses distally toward the target tissue. Furthermore, the electrode can have a distal tip that includes a small distal surface area that can securely engage the target tissue. For example, the distal tip can be a cap mounted on a distal end of the electrode pin, or an electrode helix that can be screwed into the target tissue. The electrode can therefore provide consistent and stable surface area contact between the electrode and the target tissue. Accordingly, the header assembly described below can provide controlled impedance and pacing.

Referring to FIG. 1, a perspective view of a leadless biostimulator is shown in accordance with an embodiment. A biostimulator 100 can be a leadless biostimulator, e.g., a leadless cardiac pacemaker used to deliver pacing impulses to the atria or ventricles of a heart. The biostimulator 100 can include a housing 102 having electrodes. For example, the biostimulator 100 includes each of a distal electrode 104 and a proximal electrode 106 disposed on or integrated into the housing 102. The distal electrode 104 and the proximal electrode 106 can be used to sense and pace the heart. The electrodes 104, 106 can be integral to the housing 102 or connected to the housing 102, e.g., at a distance of less than several centimeters from the housing.

In an embodiment, the housing 102 contains an energy source (not shown) to provide power to the pacing electrodes 104, 106. For example, the energy source can create a potential difference between a cathode, e.g., the distal electrode 104, and an anode, e.g., the proximal electrode 106, of the device. The energy source can be, for example, a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In one implementation, the energy source can be an energy harvesting device, such as a piezoelectric device that converts mechanical strain into electrical current or voltage. The energy source can also be an ultrasound transmitter that uses ultrasound technology to transfer energy from an ultrasound subcutaneous pulse generator to a receiver-electrode implanted on an endocardial wall.

The housing 102 can have a longitudinal axis 108, which may be an axis of symmetry along which several other biostimulator components are disposed. For example, a header assembly 110 can be mounted on a distal end of the housing 102 along the longitudinal axis 108. The header assembly 110 can include an electrical feedthrough assembly, incorporating a flange 112, a helix mount 114, and a helical fixation element 116 mounted on the helix mount 114. The assembled components of the header assembly 110, which are described further below, can provide a distal region of the biostimulator 100 that attaches to the target tissue, e.g., via engagement of the fixation element 116 with the target tissue. The distal region can deliver a pacing impulse to the target tissue, e.g., via the distal electrode 104 that is held against the target tissue, when the leadless biostimulator 100 is implanted in a surrounding environment 117, e.g., blood within an atrium or ventricle.

The housing 102 can have an electronics compartment 118 (shown by hidden lines). More particularly, the electronics compartment 118 can be a cavity laterally surrounded by a housing wall, e.g., a cylindrical wall, extending around the longitudinal axis 108. The housing wall can include a conductive, biocompatible, inert, and anodically safe material such as titanium, 316L stainless steel, or other similar materials, to laterally enclose the electronics compartment 118. More particularly, the electronics compartment 118 can be enclosed between the energy source of the biostimulator 100 (that is within a proximal portion of the housing 102) and the header assembly 110 (that is at the distal portion of the biostimulator 100). The energy source container can proximally enclose the electronics compartment 118 and the header assembly 110 can distally enclose the electronics compartment 118. The header assembly 110, the housing wall, and the energy source container can surround a volume of the electronics compartment 118.

In one implementation, the electronics compartment 118 contains an electronics assembly 120 (shown by hidden lines). The electronics assembly 120 can be mounted in the electronics compartment 118. For example, the electronics assembly 120 can include, without limitation, a flexible circuit or a printed circuit board having electrical connectors that connect to electrical pins of the header assembly 110 and the energy source. As described below, the header assembly 110 can include an electrode that connects to an electrical connector (e.g., a socket connector) of the electronics assembly 120 within the electronics compartment 118 to transmit pacing and sensing signals to and from the target tissue. The electronics assembly 120 has one or more electronic components mounted on a substrate. For example, the electronics assembly 120 can include one or more processors, capacitors, etc., interconnected by electrical traces, vias, or other electrical connectors. The electronics components can be configured to perform sensing and pacing of the target tissue.

The biostimulator components, e.g., the energy source container, the electronics compartment 118 containing the electronics assembly 120, and the header assembly 110, can be arranged on the longitudinal axis 108. Accordingly, each component can extend along the longitudinal axis 108 and have a respective axial location relative to another component along the longitudinal axis 108. For example, the energy source container can be offset from the electronics compartment 118 in a proximal direction 122 and the header assembly 110 can be offset from the electronics compartment 118 in a distal direction 124.

Figure 2:
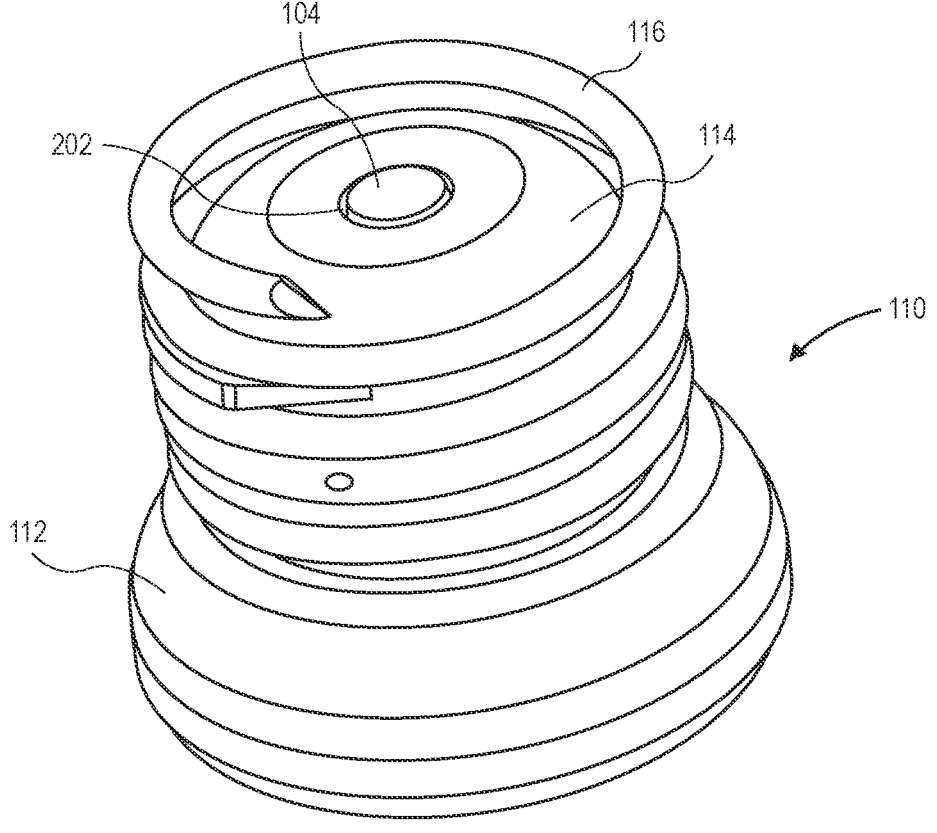
FIG. 2 is a perspective view of a header assembly having controlled therapeutic agent release, in accordance with an embodiment.

Referring to FIG. 2, a perspective view of a header assembly having controlled therapeutic agent release is shown in accordance with an embodiment. The header assembly 110 can perform several functions. First, the header assembly 110 provides for fixation of the leadless biostimulator 100 to the target tissue via the helical fixation element 116 mounted on the helix mount 114. The fixation element can be screwed into the target tissue to retain the leadless biostimulator 100 with the distal electrode 104 in contact with the target tissue. Second, the header assembly 110 provides the electrical feedthrough from the electronics compartment 118 to the surrounding environment 117 to allow for sensing and pacing of the target tissue. More particularly, the electrical feedthrough assembly of the header assembly 110 can transmit electrical pulses through the distal electrode 104 to the target tissue. Third, the header assembly 110 contains a therapeutic agent between the helix mount 114 and the flange 112 that can elute outward to the target tissue when the leadless biostimulator 100 is implanted in the surrounding environment 117. More particularly, fluid, e.g., blood, from the surrounding environment 117 can flow inward through a gap 202 between the distal electrode 104 and the helix mount 114 to a space contained axially between the helix mount 114 and the flange 112, and agent-laden fluid can then flow outward through the gap 202 toward the target tissue.

Figure 3:
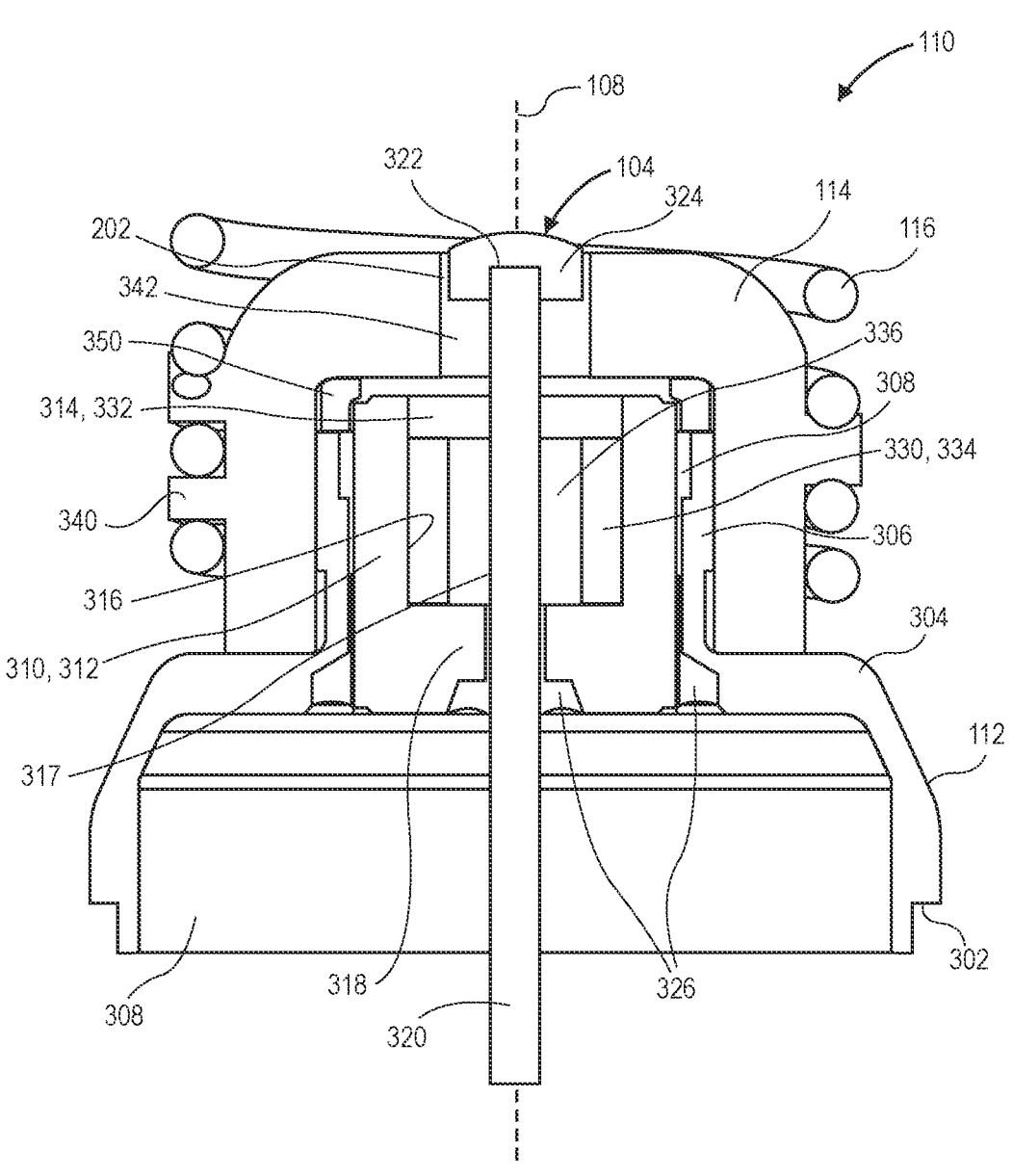
FIG. 3 is a sectional view of a header assembly having a monolithic controlled release device (MCRD) between an insulator and electrode, in accordance with an embodiment.

Referring to FIG. 3, a sectional view of a header assembly having a monolithic controlled release device (MCRD) between an insulator and electrode is shown in accordance with an embodiment. In certain implementations, each of the components of the header assembly 110 may be symmetrically formed about the longitudinal axis 108. For example, the cross-sectional area of the flange 112 illustrated in FIG. 3 can be swept about the longitudinal axis 108 such that the outer surface has a profile as shown in FIG. 2. In other implementations, the profiles of the components of the header assembly 110 may be non-cylindrical. For example, a cross-section of the flange 112 taken about a transverse plane extending orthogonal to the longitudinal axis 108 may reveal an outer surface of the flange 112 that is square, pentagonal, elliptical, etc., or any other suitable shape. Accordingly, the particular shapes illustrated in the figures are provided by way of example only and not necessarily by way of limitation.

The flange 112 can be mounted on the housing 102 (FIG. 1). For example, a proximal flange end 302, e.g., a lip, may be mounted on a distal end of the housing wall that surrounds the electronics compartment 118. The flange 112 can be connected to the housing 102 by a hermetic seal, e.g., a weld or any other similar hermetically sealed connection. For example, the hermetic weld can be formed circumferentially around a seam between the proximal flange end 302 and the distal end of the housing wall.

In an embodiment, the flange 112 includes a shoulder 304. The flange 112 can have a flange wall extending distally from the proximal flange end 302 to the shoulder 304. The shoulder 304 can be a transition region between the flange wall that extends substantially longitudinally, from the proximal flange end 302, to the flange wall that extends substantially transversely. In an embodiment, the shoulder 304 has a distal shoulder surface that extends substantially transversely, and thus, the distal shoulder surface can extend transverse to the longitudinal axis 108. Accordingly, the distal shoulder surface can face the distal direction 124. The distal shoulder surface extends radially inward toward a flange connector 306. The flange connector 306 can extend distally from the distal shoulder surface, and may receive the helix mount 114. For example, the flange connector 306 can have an external thread that couples to an internal thread of the helix mount 114.

In an embodiment, the flange 112 includes a flange channel 308 extending along the longitudinal axis 108 from the proximal flange end 302 to a distal flange end. More particularly, the flange channel 308 can be a through-hole extending entirely through the flange 112 in the longitudinal direction. The shoulder 304 of the flange 112 can extend around and circumferentially surround a proximal region of the flange channel 308. Similarly, the flange connector 306 can extend around and circumferentially surround a distal region of the flange channel 308. Accordingly, the shoulder 304 and the flange connector 306 can define the flange channel 308. The proximal region of the flange channel 308 can define a distal region of the electronics compartment 118 that contains the electronics assembly 120 when the flange 112 is mounted on the housing 102.

The header assembly 110 can include an insulator 310 in the flange channel 308. In an embodiment, the insulator 310 includes an insulator wall 312 extending around an insulator cavity 314. The insulator wall 312 can extend longitudinally from a proximal end of the insulator 310 to a distal end of the insulator 310. For example, the insulator wall 312 can be a cylindrical, annular wall having an outer insulator surface facing radially outward, and an inner insulator surface 316 facing radially inward and partially defining the insulator cavity 314. The insulator 310 can also include an insulator base 318 extending laterally at a location between the distal end and the proximal end of the insulator 310. The insulator base 318 can be a transverse wall extending across the interior of the insulator 310, orthogonal to the longitudinal axis 108. The insulator base 318 can have an upper wall surface facing distally and partially defining the insulator cavity 314 of the insulator 310. Accordingly, the insulator 310 can be mounted within the flange channel 308 to insulate the insulator cavity 314 from the metallic flange connector 306, and to provide a receptacle for a therapeutic agent, as described below.

In an embodiment, the header assembly 110 includes the electrode 104 mounted within the insulator 310 and the flange 112. More particularly, the electrode 104 extends longitudinally through the insulator cavity 314 along the longitudinal axis 108. The electrode 104 can include several components. For example, the electrode 104 can include an electrode pin 320 extending along the longitudinal axis 108 from the electronics compartment 118 through the insulator cavity 314 to a distal end 322. The distal end 322 may be located distal to the distal end of the insulator 310. In an embodiment, the electrode 104 includes an electrode tip 324 at the distal end 322. The electrode tip 324 can be a cap that is mounted on, and bonded to, the distal end 322. For example, the electrode tip 324 can include an electrode cap having a counterbore or a through-hole to receive, and be welded to, the distal, tissue-facing end of the electrode pin 320. Alternatively, the electrode tip 324 can be a portion of the electrode that is formed to have a different dimension than the electrode pin 320. For example, the electrode tip 324 can having an outer dimensions that is greater than an outer dimension of the electrode pin 320. The electrode tip 324 may therefore have a proximal surface that faces the insulator cavity 314 to restrict the elution of therapeutic agent distally from the insulator cavity 314.

The electrode tip 324 can act as the active, tissue-touching electrode to sense and deliver electrical impulses to the target tissue. In an embodiment, a distal surface area of the electrode tip 324 is sized to provide predetermined impedance parameters. The electrode 104, e.g., the pin and the cap, can be formed from platinum iridium or another biocompatible conductor. Based on the electrical properties of the electrode material, the distal surface area can be sized to provide a predetermined impedance at the contact area between the target tissue and the electrode. Generally, the smaller the distal surface area, the larger the impedance. Given that the electrode tip 324 can be formed to be quite small, and because the tip will reliably engage the target tissue over the surface area, the impedance of the electrode can be controllable and suitably high for reliable pacing. It will be appreciated that the electrical feedthrough assembly can be a filtered or unfiltered assembly, as is known in the art. More particularly, the electrical feedthrough assembly can incorporate an integral EMI filter capacitor in electrical communication with the electrode 104 (filtered feedthrough assembly) or not (unfiltered feedthrough assembly).

In an embodiment, the flange 112, the insulator 310, and the electrode 104 are joined. For example, a joint 326 can be formed between the flange 112, the insulator 310, and the electrode 104 to fasten the components together and to provide a hermetic seal between the flange channel region proximal to the insulator 310 (e.g., the electronic compartment) and the flange channel region distal to the insulator 310. In an embodiment, the joint 326 is a brazed joint, e.g., a gold brazed joint, which radially surrounds a portion of the components to fill gaps between the components and form the hermetic joint. The electrode 104 can pass through the joint 326, and through a hole in the insulator base 318, to transfer electrical signals between the target tissue and the internal circuitry of the leadless biostimulator 100.

In an embodiment, the header assembly 110 includes a MCRD 330. The MCRD 330 can be an agent-containing filler that is located in the insulator cavity 314. For example, the MCRD 330 can include a therapeutic agent loaded into a matrix or solid composition. In at least one implementation, the therapeutic agent can include a corticosteroid, such as dexamethasone sodium phosphate, dexamethasone acetate, etc. When the therapeutic agent is consistently released into the target tissue at a controlled dose, the agent can reduce inflammation associated with the device implantation.

The MCRD 330 can be placed or located in the insulator cavity 314 radially inward from the insulator wall 312 and distal to the insulator base 318. Elution of the therapeutic agent from the MCRD 330 can be controlled by a geometry of the MCRD 330, as well as by the ingress and egress of fluid, e.g., blood, from the surrounding environment 117 into the insulator cavity 314. Accordingly, the header assembly 110 can be configured to allow for fluid transport between the MCRD 330 and the surrounding environment 117 through the insulator cavity 314. A specified dose of the therapeutic agent may therefore flow, or weep, from the MCRD 330 through the insulator cavity 314 and the helix mount 114 to the target tissue at an implantation site of the biostimulator 100 within a patient.

In an embodiment, the MCRD 330 is in fluid communication with a space 332 between the insulator 310 and the electrode 104 to elute the therapeutic agent into the space 332 when the leadless biostimulator 100 is implanted in blood. The space 332 can be between the inner insulator surface 316 and an outer electrode surface 317 of the electrode 104. More particularly, the space 332 can be defined radially between the inner insulator surface 316 and the outer electrode surface 317. Furthermore, the space 332 can be defined longitudinally between the insulator base 318 and a distal end of the insulator 310. Accordingly, in an embodiment, the space 332 is an annular region of the insulator cavity 314 defined between the electrode 104 and the insulator 310.

In an embodiment, the MCRD 330 can be received within the space 332. For example, the MCRD 330 can have an annular body 334 that is located between the electrode 104 and the insulator 310 within the insulator cavity 314, and thus, may be positioned within the space 332. The annular body 334 can include an outer surface and an inner surface that are generally cylindrical and extend between proximal and distal ends 322 of the MCRD 330. The inner surface of the MCRD 330 can define a central lumen 336 that extends longitudinally through the MCRD 330. In an embodiment, the central lumen 336 receives the electrode 104. For example, the electrode pin 320 can extend longitudinally through the central lumen 336 to the distal end 322 that is distal to the distal end of the MCRD 330. Therapeutic agent eluted from the MCRD 330 is therefore initially in the space 332 between the electrode pin 320 and the inner surface of the insulator 310. The therapeutic agent, after elution, can be carried outward by blood transfer to the surrounding environment 117.

The header assembly 110 can include the helix mount 114. The helix mount 114 may be formed from an insulating material, such as a ceramic material (e.g., alumina, ruby, glass, or another ceramic insulating material) and/or a non-ceramic material (e.g., polyetheretherketone (PEEK)). The helix mount 114 can be mounted on the flange 112. For example, the helix mount 114 can have an inner surface that is threaded to engage external threads of the flange connector 306. The helix mount 114 may also include an external threaded feature. More particularly, the helix mount 114 can include a mount flange 340, which may be a helical ledge extending around an outer surface of the helix mount 114. The mount flange 340 can receive the helical fixation element 116. More particularly, the helical fixation element 116 can be mounted on the helix mount 114 by screwing the fixation element onto the helical ledge until a distal tip of the fixation element is properly located for tissue engagement.

In an embodiment, the helix mount 114 includes a helix mount channel 342 through which therapeutic agent can be eluted when the leadless biostimulator 100 is implanted in blood. The helix mount channel 342 can be a hole extending through a distal wall of the helix mount 114. The hole can be centrally located, e.g., along the longitudinal axis 108, such that the helix mount channel 342 is concentric with the electrode pin 320 and/or the electrode tip 324. Furthermore, the helix mount channel 342 can have a hole dimension that is larger than the electrode pin 320 and the electrode tip 324 such that the annular gap 202 is formed between the helix mount 114 and the electrode 104. More particularly, the annular gap 202 can be a gap formed around the electrode 104 and extending from the insulator cavity 314 to the surrounding environment 117 to provide an elution path for the therapeutic agent to be transferred through. Accordingly, when the leadless biostimulator 100 is implanted, blood can enter the insulator cavity 314 through the annular gap 202 to dissolve the therapeutic agent and transfer the drug-laden agent through the space 332 and the helix mount channel 342 to the surrounding environment 117. Advantageously, the annular gap 202 may be less likely to clog than a single small hole, and thus, may promote consistent and continuous elution of the therapeutic agent into the target tissue.

The flange 112 may be a portion of the proximal electrode 106, and thus, the electrical feedthrough assembly of the header assembly 110 may also include the proximal electrode 106. In such case, the electrodes (the electrode tip 324 and the flange 112) may be in close proximity, separated by an electrode gap extending radially between the flange connector 306 and the electrode 104. If blood were allowed to fill the electrode gap between the flange 112 and the electrode 104, the electrodes 104, 106 could be electrically shorted and pacing impulses may not properly pace the cardiac tissue. Accordingly, a barrier can be included in the biostimulator 100 to prevent blood from filling the electrode gap and/or to block an electrical path between the flange 112 and the electrode 104. In an embodiment, the barrier includes a gasket 350. The gasket 350 can be an annular seal that is pressed between a distal end of the flange connector 306 and the insulator 310, and a proximal inner surface of the helix mount 114. The gasket 350 bridges the gap between the insulative helix mount 114 and insulator 310, and thus, blood that enters the insulator cavity 314 to facilitate therapeutic agent release does not contact the flange 112.

In an embodiment, the MCRD 330 is retained in part by the electrode 104. For example, the electrode tip 324 can have an outer dimension that is greater than a dimension of the MCRD 330 central lumen 336. Accordingly, the MCRD 330 may be restrained from sliding off of the electrode 104 into the surrounding environment 117. Furthermore, an inner dimension of the helix mount channel 342 may be less than a dimension of the central lumen 336 of the MCRD 330. Accordingly, the MCRD 330 may be restrained from sliding out of the insulator cavity 314 by the helix mount 114.

Instead of or in addition to the retention features described above, the MCRD 330 may be partly retained via a press fit against one or more of the insulator 310 or the electrode 104. More particularly, the outer surface of the MCRD 330 may press against the inner insulator surface 316 of the insulator 310 and/or the inner surface of the MCRD 330 may press against the outer electrode surface 317. Accordingly, friction caused by a press fit between the MCRD 330 and one or more of the insulator 310 or the electrode 104 can retain the MCRD 330 within the insulator cavity 314. In an embodiment, at least one of the side surfaces of the MCRD 330 has a clearance with an opposing surface of the insulator 310 or the electrode 104. For example, when the MCRD 330 is press fit against the insulator 310, the MCRD 330 may have a clearance fit with the electrode 104 (FIG. 3). The clearance can maximize the MCRD surface area exposed to blood after implantation to promote elution of the therapeutic agent into the space 332.

Optionally, the MCRD 330 can include a time-release coating. The time-release coating may be applied, e.g., by spray or dip coating, to an exterior surface of the MCRD 330. The time release coating can be an absorbable coating, such as a hydrophilic coating, that absorbs within minutes to an hour of being in contact with blood. Accordingly, the exterior surface can contact blood when the biostimulator 100 is implanted, and the release of therapeutic agent can be delayed while the coating dissolves. After the coating dissolves, the therapeutic agent can elute from the MCRD 330 and follow an elution path through the space 332 and the helix mount channel 342 toward the surrounding environment 117.

Figure 4:
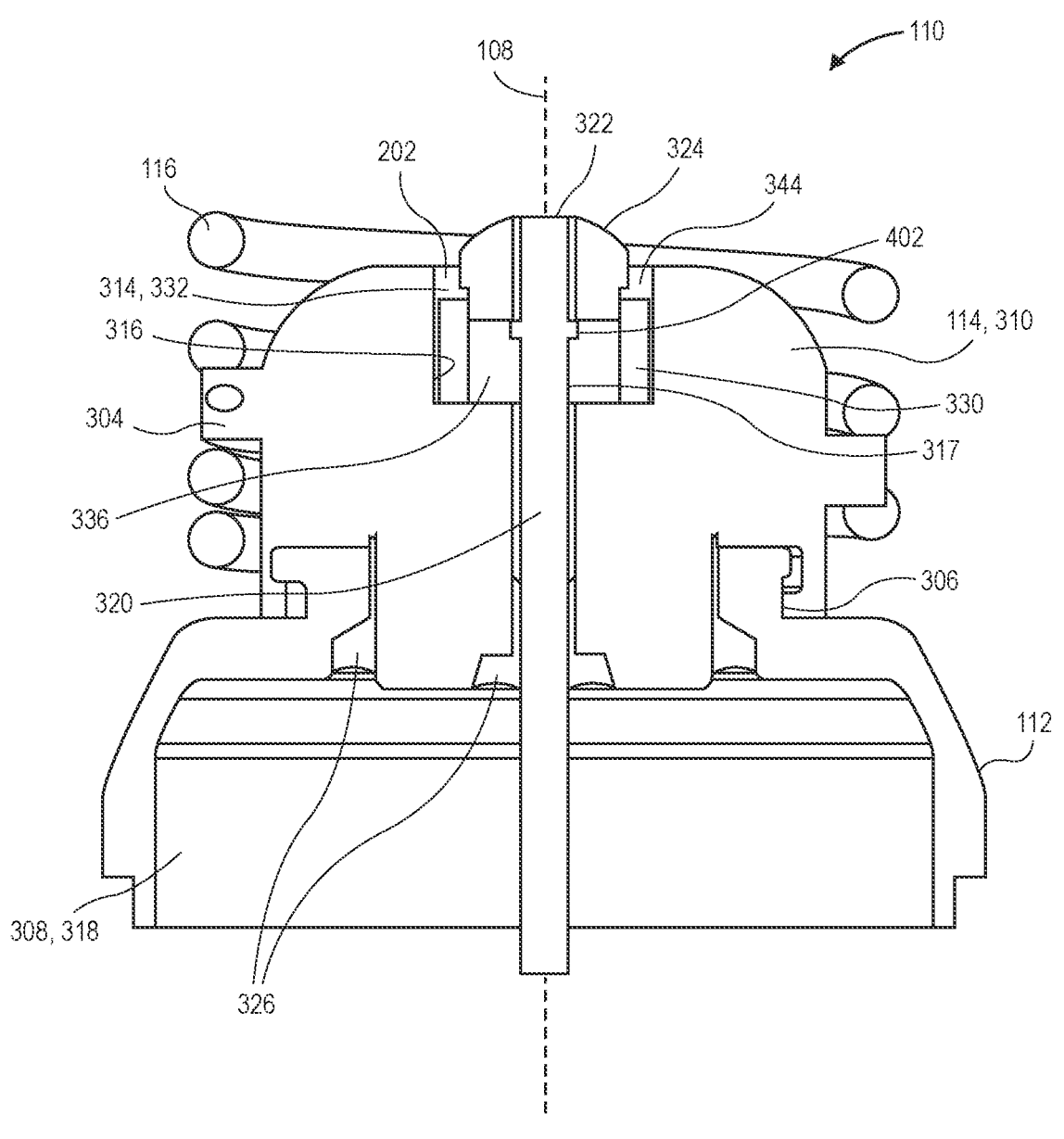
FIG. 4 is a sectional view of a header assembly having a MCRD in an insulator cavity of a ceramic helix mount, in accordance with an embodiment.

Referring to FIG. 4, a sectional view of a header assembly having a MCRD in an insulator cavity of a ceramic helix mount is shown in accordance with an embodiment. The header assembly 110 can include a helix mount 114 that combines features of the insulator 310 and the helix mount 114 described above with respect to FIG. 3. More particularly, in an embodiment, the insulator 310 and the helix mount 114 are monolithically formed from ceramic. The fully-ceramic helix mount 114 can connect to the flange 112 via a threaded or threadless connector that attaches the flange connector 306 to the helix mount 114. For example, the helix mount 114 can be screwed onto the flange connector 306 to secure the flange 112 to the helix mount 114. Similarly, the fixation element can be screwed onto the mount flange 340.

In an embodiment, the helix mount 114 can have a hole extending from a proximal end of the helix mount 114 to a distal end of the helix mount 114. The electrode 104 can be inserted into the hole, and secured by the joint 326, as described above. More particularly, the joint 326 can be a brazed joint securing and sealing the electrode 104 to the helix mount 114. Accordingly, the header assembly 110 can include the flange 112, the helix mount 114 (which incorporates the insulator 310), and the electrode 104 securely fastened to each other and hermetically sealed to prevent ingress of blood from the surrounding environment 117 into the electronics compartment 118.

The insulator cavity 314 can be formed directly into the helix mount 114. More particularly, a counterbore can be formed in a distal end of the fully-ceramic helix mount 114 such that the counterbore includes the inner insulator surface 316. When the electrode 104 is secured relative to the helix mount 114, the inner insulator surface 316 faces the outer electrode surface 317, providing the space 332 between the insulator 310 and the electrode 104. The MCRD 330 can be loaded into the space 332, and thus, can elute therapeutic agent into the space 332 when the biostimulator 100 is implanted in blood.

The electrode 104 may include a through-post configuration. The through-post configuration includes an electrode tip 324 having a through-hole to receive the electrode pin 320. More particularly, when the electrode pin 320 is inserted into the through-hole of the electrode tip 324, the distal end 322 of the electrode pin 320 can be exposed to the surrounding environment 117.

In an embodiment, the electrode pin 320 includes a stop 402 to provide a positional reference to the electrode tip 324. The stop 402 can include a protuberance or a ledge extending radially from the longitudinal pin of the electrode 104. An outer dimension of the stop 402 may be greater than an inner dimension of the electrode tip through-hole, and thus, when the electrode tip 324 is inserted over the distal end 322 of the electrode pin 320, the electrode tip 324 can rest on the stop 402. The electrode tip 324 may then be welded or otherwise attached to the electrode pin 320 to form the electrode 104.

As described above, the MCRD 330 can be located within the insulator cavity 314 between the electrode 104 and the insulator 310. For example, an inner dimension of the MCRD 330 extending around the central lumen 336 may be less than an outer dimension of the electrode tip 324. Thus, the electrode tip 324 can retain the MCRD 330 within the space 332 of the insulator cavity 314. Also as described above, the MCRD 330 can elute therapeutic agent through the space 332 and through the annular gap 202 to the surrounding environment 117 when the biostimulator 100 is implanted in blood.

Combining the insulator 310 and the helix mount 114 in a fully-ceramic helix mount 114, as described above, can reduce an overall height of the header assembly 110. As illustrated, with the fully ceramic helix mount 114, the height of the flange connector 306 and the height of the helix mount 114 can be reduced, which shortens the header assembly 110. Advantageously, by shortening the header assembly 110, the device length may instead be devoted to extending a length of the energy source. Accordingly, an energy capacity and operational longevity can be extended as compared to biostimulators 100 having non-integrated helix mount 114 and insulator 310 components.

Figure 5:
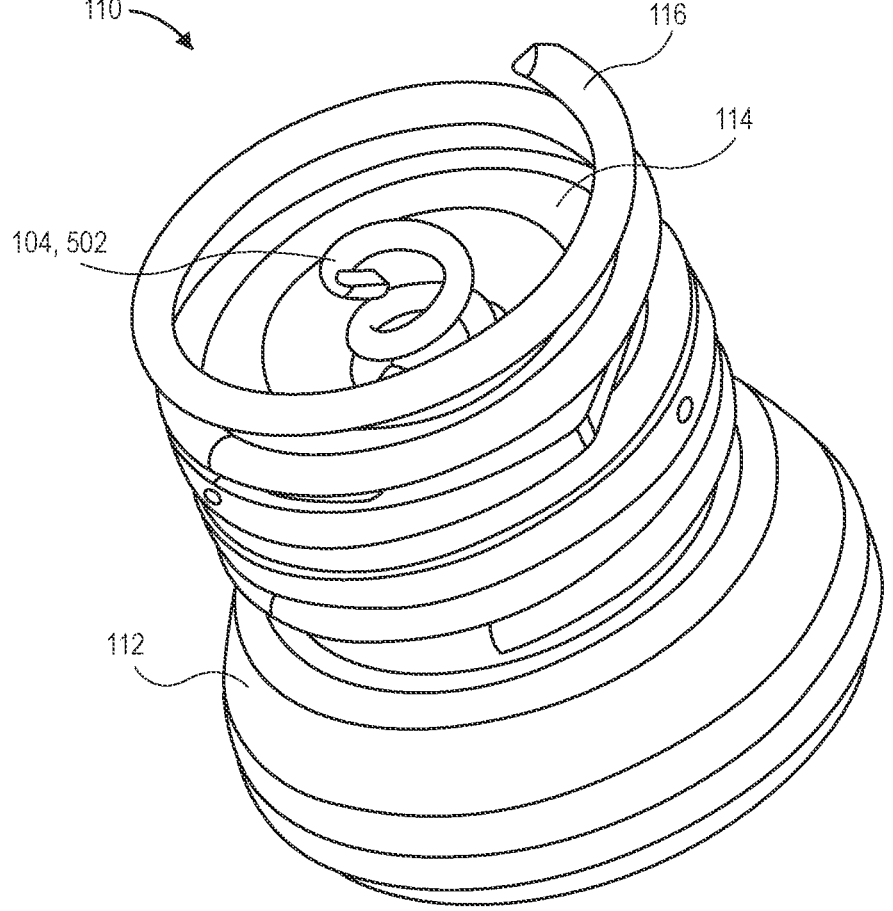
FIG. 5 is a perspective view of a header assembly having controlled therapeutic agent release, in accordance with an embodiment.

Referring to FIG. 5, a perspective view of a header assembly having controlled therapeutic agent release is shown in accordance with an embodiment. The header assembly 110 can include a fully-ceramic helix mount 114, as described above. In an embodiment, the electrode 104 of the header assembly 110 includes an electrode helix 502. The electrode helix 502 can provide a distal portion of the electrode 104. More particularly, the electrode helix 502 can be a portion of the electrode 104 that engages tissue during implantation. For example, the electrode helix 502 can be coaxial with the helical fixation element 116 and, during implantation, both the helical fixation element 116 and the electrode helix 502 can be screwed into the target tissue.

An electrode helix 502, like the electrode tip 324 described above, can provide controlled impedance for reliable pacing. In the case of the electrode helix 502, the electrode 104 can be securely and predictably engaged with the target tissue by virtue of the electrode anchoring within the tissue. The anchored electrode can provide consistent tissue contact from case to case, and may therefore provide for more predictable impedance between the electrode and the tissue. Accordingly, the helical electrode can provide more consistent impedance and pacing.

Figure 6:
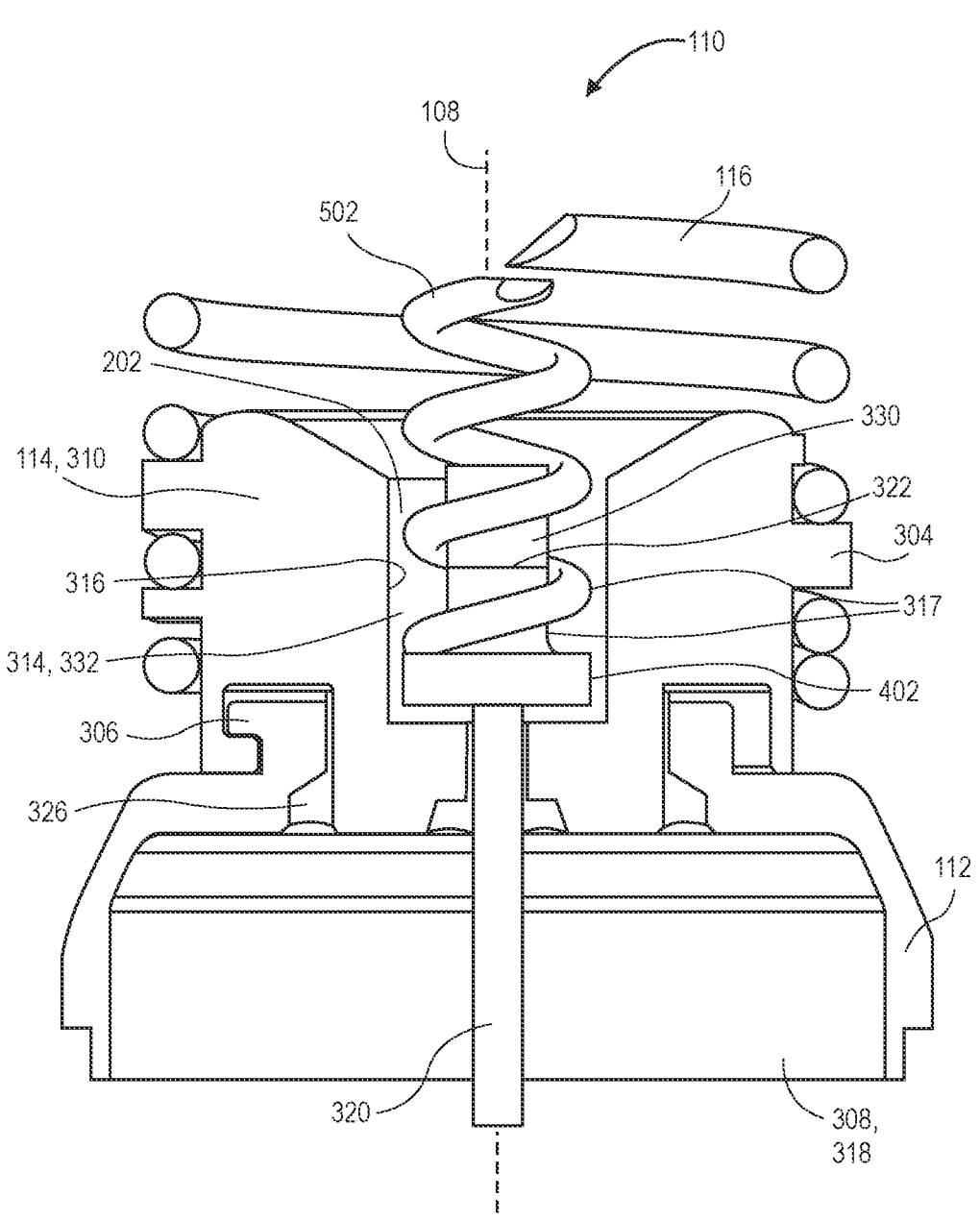
FIG. 6 is a sectional view of a header assembly having a MCRD within an electrode helix, in accordance with an embodiment.

Referring to FIG. 6, a sectional view of a header assembly having a MCRD within an electrode helix is shown in accordance with an embodiment. Several features of the embodiment shown in FIG. 6 are similar to those described above with respect to FIGS. 3 and 4, and thus, are not described again in the interest of brevity.

The electrode pin 320 can extend longitudinally through the insulator cavity 314. In an embodiment, the electrode helix 502 is mounted on the electrode pin 320. For example, the electrode helix 502 can be slipped over and mounted on the distal end 322 of the electrode pin 320. The electrode pin 320 may include the stop 402, and thus, the electrode helix 502 can rest on the stop 402. The electrode helix 502 may therefore be welded to the electrode pin 320 in a consistent manner. More particularly, the stop 402 can provide a positional reference to ensure that the electrode helix 502 is properly located relative to the fixation element. The electrode pin 320 and the electrode helix 502 may therefore be joined to form the electrode 104 that carries electrical signals between the electronics compartment 118 and the target tissue that the electrode helix 502 is screwed into.

In an embodiment, the MCRD 330 has a cylindrical shape. More particularly, the MCRD 330 can be a cylindrical plug, having no central channel, and may be inserted into the inner lumen of the electrode helix 502. Alternatively, the MCRD 330 can have the annular or ring-shaped structure described above, and may be loaded into the electrode helix 502. The plug can be press fit within the electrode helix 502. Accordingly, the press fit between the electrode helix 502 and the MCRD 330 can retain the MCRD and prevent dislodgement of the MCRD from the insulator cavity 314.

It will be appreciated that, although the MCRD 330 is radially inward from the electrode helix 502 (rather than being radially outward from the electrode pin 320 as shown in FIGS. 3-4), the MCRD 330 can still elute therapeutic agent along an elution path that passes through the space 332 between the insulator 310 and the electrode 104. More particularly, when blood enters the insulator cavity 314, the therapeutic agent can be dissolved and flow radially outward from the inner lumen of the helix through the helical turns into the space 332 between the outer electrode surface 317 of the helical turns and the inner insulator surface 316 of the helix mount 114. From the space 332, the therapeutic agent can travel distally outward from the insulator cavity 314 into the surrounding environment 117 through the annular gap 202. Advantageously, elution through the space 332 can allow for the therapeutic agent to be released controllably through the annular gap 202 that is larger and less likely to be clogged than a single hole in an electrode cup, for example.

Figure 7:
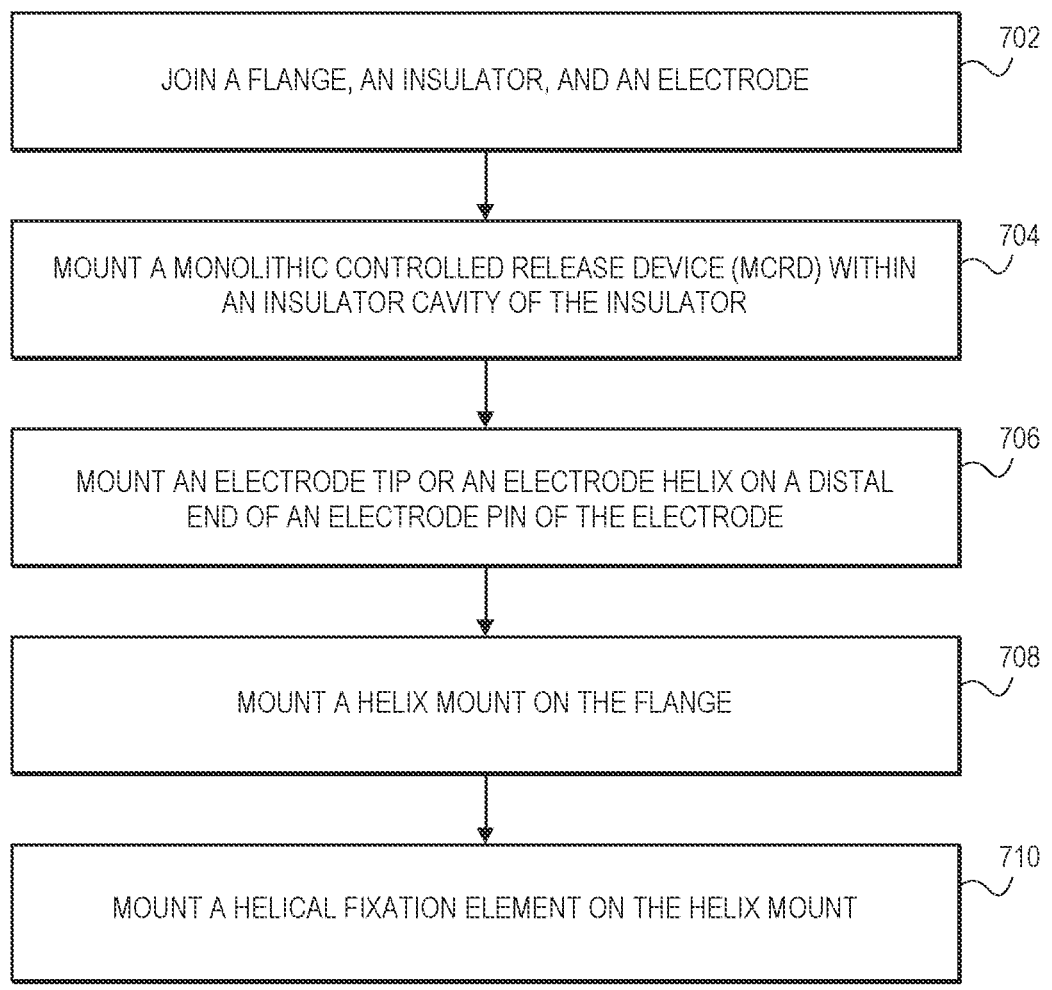
FIG. 7 is a flowchart of a method of manufacturing a leadless biostimulator, in accordance with an embodiment.

Referring to FIG. 7, a flowchart of a method of manufacturing a leadless biostimulator is shown in accordance with an embodiment. As a preliminary operation, the insulator 310 can be loaded into the flange channel 308 such that the insulator cavity 314 and the flange channel 308 are concentric. The insulator 310 may have a thin, metallic coating deposited on its outer surface to allow for a brazing process to be performed on it, as described below. The electrode 104 can be loaded into the concentrically arranged flange channel 308 and insulator cavity 314. More particularly, the electrode pin 320 can be inserted into the hole in the insulator base 318 such that the electrode 104 extends longitudinally through the insulator cavity 314. The electrode pin 320 can be cut to a length (before or after loading the electrode into the assembly) such that the electrode pin 320 extends to a predetermined length distal to and proximal to the insulator base 318. The distal portion of the electrode pin 320 can have a length to align the distal end 322 of the pin with the helix mount channel 342. The proximal region of the electrode pin 320 can have a length to extend to a proximal end of the pin that will engage the electronics assembly 120 in the electronics compartment 318.

At operation 702, the flange 112, the insulator 310, and the electrode 104 are joined together. The concentrically arranged components can be secured by the joint 326. In an embodiment, gold is flowed into the junctions between the components in a brazing process. The molten gold can be cooled to braze the components together to provide a hermetic seal through which the electrode 104 can pass electrical signals.

At operation 704, the MCRD 330 is mounted within the insulator cavity 314. In an embodiment, the MCRD 330 can be loaded over the electrode 104, e.g., by inserting the electrode pin 320 through the central channel of the annular MCRD 330. Alternatively, the MCRD 330 can be loaded into the electrode 104, e.g., by sliding the MCRD 330 into an interior lumen of the electrode helix 502.

After loading the MCRD 330 into the insulator cavity 314, the MCRD 330 can be retained to a degree. For example, the MCRD 330 can form a press fit to one or more of the insulator wall 312, the electrode pin 320, or the electrode helix 502, depending upon the header assembly configuration being manufactured. At operation 706, the MCRD 330 may be further retained. More particularly, the electrode tip 324 or the electrode helix 502 can be mounted on the distal end 322 of the electrode pin 320 to retain the MCRD 330 within the insulator cavity 314. In the case of the electrode tip 324, the electrode 104 can include a cap that has a larger outer dimension than the central lumen 336 of the MCRD 330, and thus, the cap can resist distal movement of the MCRD 330 from the electrode pin 320. In the case of the electrode helix 502, the MCRD 330 can be press fit within the interior of the helix. The electrode helix 502 can be connected, e.g., welded, to a distal end 322 of the electrode pin 320, and thus, the electrode helix 502 can resist distal movement of the MCRD 330 relative to the electrode pin 320. In either case, the electrode features can both retain the MCRD 330 within the insulator cavity 314 and provide electrical conduction of pacing signals to the target tissue.

The operations of the method may be performed in an alternative order. For example, for the header assembly configuration shown in FIG. 6, the operation of mounting (and optionally welding) the electrode helix 502 on the electrode pin 320 at operation 706 may precede the operation of loading the MCRD 330 into the electrode helix 502 (and the insulator cavity 314) at operation 704. Accordingly, it will be appreciated that the operations may be reordered, omitted, or modified as needed to manufacture the header assembly configurations described above.

At operation 708, the helix mount 114 is mounted on the flange 112. The helix mount 114 can be fastened to the flange connector 306, e.g., by engaging mating threads of the components. Alternatively, other fasteners can secure the helix mount 114 to the flange 112. When the helix mount 114 is attached to the flange 112, the helix mount channel 342 can be positioned to receive the electrode 104, e.g., the electrode tip 324, such that the gap 202 provides an elution pathway between the insulator cavity 314 within the header assembly 110 and the surrounding environment 117. The gap 202 can be sized to achieve good fluid exchange between the interior and the exterior of the header assembly 110.

At operation 710, the helical fixation element 116 is mounted on the helix mount 114. The helical fixation element 116 can be screwed onto the mount flange 340. Optionally, the fixation element can be adhered to the mount flange 340 by a thermal or adhesive weld. Accordingly, the fixation element can be secured to the helix mount 114 to retain the header assembly 110 against the target tissue when the fixation element is screwed into the target tissue during device implantation.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A header assembly for a leadless biostimulator, comprising:
   a flange including a flange channel extending along a longitudinal axis;
   an insulator in the flange channel and including an insulator cavity;
   an electrode extending longitudinally through the insulator cavity; and
   a monolithic controlled release device (MCRD) in the insulator cavity, wherein the MCRD is in a space radially between the insulator and the electrode to elute therapeutic agent directly into the space when the leadless biostimulator is implanted.

2. The header assembly of claim 1, wherein the space is between an inner insulator surface of the insulator and an outer electrode surface of the electrode within the insulator cavity.

3. The header assembly of claim 1, wherein the MCRD has an annular body including a central lumen, and wherein the electrode extends longitudinally through the central lumen.

4. The header assembly of claim 1, wherein the electrode includes an electrode pin extending longitudinally through the insulator cavity, and an electrode tip mounted on a distal end of the electrode pin.

5. The header assembly of claim 1, wherein the electrode includes an electrode pin extending longitudinally through the insulator cavity, and an electrode helix mounted on a distal end of the electrode pin.

6. The header assembly of claim 1 further comprising:
   a helix mount mounted on the flange, wherein the helix mount includes a helix mount channel in fluid communication with the space such that the therapeutic agent elutes through the space and the helix mount channel to a surrounding environment when the leadless biostimulator is implanted; and
   a helical fixation element mounted on the helix mount.

7. The header assembly of claim 6, wherein the helix mount channel includes an annular gap between the helix mount and the electrode.

8. The header assembly of claim 6, wherein the insulator and the helix mount are monolithically formed from ceramic.

9. The header assembly of claim 1, wherein the MCRD is press fit against one or more of the insulator or the electrode.

10. A leadless biostimulator, comprising:

a housing having an electronics compartment containing an electronics assembly;

a flange mounted on the housing and including a flange channel extending along a longitudinal axis;

an insulator in the flange channel and including an insulator cavity;

an electrode extending longitudinally through the insulator cavity; and a monolithic controlled release device (MCRD) in the insulator cavity, wherein the MCRD is in a space radially between the insulator and the electrode to elute therapeutic agent directly into the space when the leadless biostimulator is implanted.

11. The leadless biostimulator of claim 10, wherein the space is between an inner insulator surface of the insulator and an outer electrode surface of the electrode within the insulator cavity.

12. The leadless biostimulator of claim 10, wherein the MCRD has an annular body including a central lumen, and wherein the electrode extends longitudinally through the central lumen.

13. The leadless biostimulator of claim 10, wherein the electrode includes an electrode pin extending longitudinally through the insulator cavity, and an electrode tip mounted on a distal end of the electrode pin.

14. The leadless biostimulator of claim 10, wherein the electrode includes an electrode pin extending longitudinally through the insulator cavity, and an electrode helix mounted on a distal end of the electrode pin.

15. The leadless biostimulator of claim 10 further comprising:

a helix mount mounted on the flange, wherein the helix mount includes a helix mount channel in fluid communication with the space such that the therapeutic agent elutes through the space and the helix mount channel to a surrounding environment when the leadless biostimulator is implanted; and a helical fixation element mounted on the helix mount.

16. The leadless biostimulator of claim 15, wherein the helix mount channel includes an annular gap between the helix mount and the electrode.

17. A method of manufacturing a leadless biostimulator, comprising:

joining a flange, an insulator, and an electrode such that the electrode extends along a longitudinal axis through a flange channel of the flange and an insulator cavity of the insulator; and mounting a monolithic controlled release device (MCRD) within the insulator cavity, wherein the MCRD is in a space radially between the insulator and the electrode to elute therapeutic agent directly into the space when the leadless biostimulator is implanted.

18. The method of claim 17, wherein the MCRD has an annular body including a central lumen, and wherein the electrode extends longitudinally through the central lumen.

19. The method of claim 17 further comprising mounting an electrode tip or an electrode helix on a distal end of an electrode pin of the electrode.

20. The method of claim 17 further comprising:

mounting a helix mount on the flange, wherein the helix mount includes a helix mount channel in fluid communication with the space such that the therapeutic agent elutes through the space and the helix mount channel to a surrounding environment when the leadless biostimulator is implanted; and mounting a helical fixation element on the helix mount.

* * * * *